(12) United States Patent
Miki et al.

(10) Patent No.: US 7,862,905 B2
(45) Date of Patent: Jan. 4, 2011

(54) ARYLAMINE COMPOUND AND ORGANIC ELECTROLUMINESCENT DEVICE

(75) Inventors: Tetsuzo Miki, Ibaraki (JP); Naohiro Tarumoto, Ibaraki (JP); Yoshio Taniguchi, Nagano (JP); Musubu Ichikawa, Nagano (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 802 days.

(21) Appl. No.: 10/594,239

(22) PCT Filed: Mar. 25, 2005

(86) PCT No.: PCT/JP2005/006426

§ 371 (c)(1),
(2), (4) Date: Jun. 14, 2007

(87) PCT Pub. No.: WO2005/094133

PCT Pub. Date: Oct. 6, 2005

(65) Prior Publication Data

US 2007/0285004 A1    Dec. 13, 2007

(30) Foreign Application Priority Data

Mar. 25, 2004  (JP)  .................. P. 2004-089836
Mar. 25, 2004  (JP)  .................. P. 2004-090334

(51) Int. Cl.
*H01J 1/63* (2006.01)
(52) U.S. Cl. .................. 428/690; 313/504; 548/444
(58) Field of Classification Search .................. None
See application file for complete search history.

(56) References Cited

FOREIGN PATENT DOCUMENTS

EP    0 508 562 A1    10/1992

(Continued)

OTHER PUBLICATIONS

English Translation of JP 10-284252.*
English Translation of JP 2000-063335.*
Louie J. and Hartwig J.F., Discrete High Molecula Weight Triarylamine Dendrimers Prepared by Palladium-Catalyzed Amination, J. Am. Chem. Soc., 1997, pp. 11695-11696; Fig. 3.

(Continued)

*Primary Examiner*—D. Lawrence Tarazano
*Assistant Examiner*—Gregory Clark
(74) *Attorney, Agent, or Firm*—Oblon, Spivak, McClelland, Maier & Neustadt, L.L.P.

(57) ABSTRACT

The present invention provides an arylamine compound having a molecular weight of from 1500 to 6000 represented by the general formula (1):

According to the present invention, there can be provided an arylamine compound having excellent hole injection and transporting characteristics and being capable of forming a stable thin film. By using the compound, emission efficiency and durability of conventional organic EL devices can remarkably be improved.

8 Claims, 8 Drawing Sheets

FOREIGN PATENT DOCUMENTS

| | | |
|---|---|---|
| JP | 04-308688 | 1/1992 |
| JP | 03-3194657 | 10/1993 |
| JP | 07-097355 | 4/1995 |
| JP | 08-03122 | 1/1996 |
| JP | 08-48656 | 2/1996 |
| JP | 03-75955 | 3/1996 |
| JP | 8-259934 | 10/1996 |
| JP | 10-284252 | * 10/1998 |
| JP | 2000-63335 | 2/2000 |
| JP | 2000-063335 | * 2/2000 |

OTHER PUBLICATIONS

Hartwig J. F., Palladium-Catalyzed synthesis of Triarylamine Macromolecules, Polymer Preprints (American Chemical Society, Division of Polymer Chemistry), 41(1), 2000, pp. 420-421.

Hartwig J.F., et al. The Synthesis of Triary Lamine Macromolecules by Palladium-Catalyzed Amination of Aryl Halides, Polymeric Materials Science and Engineering, 80, 1999, pp. 41 to 42.

Tokito, S., et al., Temperature Dependences of Electroluminescent Characteristics in the Devices Fabricated with Novel Triphenylamine Derivatives, IEEE Transactions on Electron Devices, 44(8), 1997, pp. 1239 to 1244, Abstract, Figs. 1, 5.

Appl. Phys. Lett. 71(1), Jul. 7, 1997, Operating Stability of Light-Emitting Polymer Diodes Based on Poly(P-Phenylene Vinylene), J.C. Carter, et al.

Optical Materials 9, (1998), pp. 125-133, Stability of Polymer LEDs, Jeroen Vleggaar, et al.

M & BE Association, vol. 11, No. 1, pp. 32-41 (2000).

U.S. Appl. No. 12/065,417, filed Feb. 29, 2008, Miki et al.

U.S. Appl. No. 10/549,239, filed Jun. 14, 2007, Miki et al.

* cited by examiner

ARYLAMINE COMPOUND AND ORGANIC ELECTROLUMINESCENT DEVICE

TECHNICAL FIELD

The present invention relates to a compound and a device, suitable to an organic electroluminescence (EL) device which is a self-luminescent device suitable to various display devices, and particularly the invention relates to an arylamine compound having a molecular weight of from 1500 to 6000, and an organic EL device using the compound.

BACKGROUND ART

Because an organic EL device is a self-luminescent device, it is luminous, excellent in visibility, and capable of giving clear display, as compared with a liquid crystal device. Therefore, active investigations have been made.

C. W. Tang et al. of Eastman Kodak Company developed a two-layer type laminated structure element in 1987, and this enabled an organic EL device using an organic substance to be put into practical use. They laminated an electron transporting fluorescent substance and a hole transporting organic substance, and injected both charges in a layer of the fluorescent substance to make the layer emit, thereby making it possible to attain high luminance of 1,000 cd/m$^2$ or more at a voltage of 10V or lower (for example, see Patent Document 1 and Patent Document 2).

Patent Document 1: JP-A-8-48656
Patent Document 2: Japanese Patent No. 3194657

From differences in process of device preparation and characteristics of materials, organic EL devices are classified into a deposition type device using a low molecular weight material and a coating type device mainly using a high molecular weight material.

The deposition type device requires a vacuum deposition apparatus for film formation. The coating type device easily conducts film formation by applying a coating liquid to a substrate, and removing a solvent in the coating liquid, so that the production process is simple, and the production can be carried out at low cost. Coating can be conducted with an ink jet method, a spray coating method or a printing method, and expensive facilities are not necessary for the production.

General materials used in the preparation of the coating type device were polymer materials such as poly(1,4-phenylenevinylene) (hereinafter referred to as PPV) (for example, see Non-Patent Document 1).

Non-Patent Document 1: Applied Physics Letters 71-1, page 34 (1997)

An organic EL device is investigated in which the role of two layers is further finely divided, and separately from an emission layer, a hole injecting layer, a hole transporting layer and an electron transporting layer are provided. As hole injecting or transporting materials for the preparation of the hole injecting layer or the hole transporting layer by coating, poly(ethylenedioxythiophene)/poly(styrenesulfonate) (hereinafter referred to as PEDOT/PSS) is widely used (for example, see Non-Patent Document 2).

Non-Patent Document 2: optical Materials 9 (1998) 125

However, the PEDOT/PSS coating liquid is an aqueous gel dispersion hydrated with PSS, to which the molecular chain of PEDOT gives ionic interaction, and is therefore an acidic aqueous solution. For this reason, there is the difficulty on use such that the coating liquid corrodes a coating or printing apparatus such as an ink jet ejection head.

Further, it is pointed out that PSS in the coating film adversely affects an anode, and water used in the coating liquid remains in the device, leading to deterioration during driving. Additionally, it is said that a thiophene ring of PEDOT is reduced by electron influx. Due to those difficulties, it is not considered that PEDOT/PSS is a sufficient hole injecting and transporting material, and satisfactory device characteristics, particularly in durability, were not obtained.

On the other hand, as a hole injecting and transporting material in the deposition type device, copper phthalocyanine, and MTDATA represented by the following formula:

or its derivative (for example, see Patent Document 3) are proposed, but those cannot form a stable thin film by coating.

Patent Document: JP-A-4-308688

Further, to enhance durability of the organic EL device, it is considered to be good to use a compound having good thin film stability. Compounds having higher amorphous property gives higher thin film stability, and a glass transition point (Tg) is used as a measure of the amorphous property (for example, see Non-Patent Document 3).

Non-Patent Document 3: M & BE Association, Vol. 11, No. 1, pages 32-41, (2000), The Japan Society of Applied Physics.

It is considered that higher glass transition point (Tg) is better. However, glass transition point of MTDATA is 76° C., and it is not said that its amorphous property is high. Due to this, satisfactory device characteristics were not obtained in durability of the organic EL device and also in emission efficiency due to hole injecting and transporting characteristics.

DISCLOSURE OF THE INVENTION

Problems that the Invention is to Solve

One object of the present invention is to provide a homogeneous compound having excellent hole injecting and transporting properties and having excellent amorphous property as a material for an organic EL device of high efficiency and high durability.

Another object of the present invention is to provide an organic EL device of high efficiency and high durability using the compound.

As physical characteristics of a compound suitable for the present invention, there can be exemplified that (1) it has high amorphous property and is suitable for film formation by coating, (2) it has excellent hole injecting ability, (3) it has a hole transporting ability, and (4) it has a glass transition point of 150° C. or higher, and is stable in a thin film state. Further, as physical characteristics of a device suitable to the present invention, there can be exemplified that (1) film formation can be conducted by coating, (2) its emission efficiency is high, (3) its maximum emission luminance is high, and (4) a laminated device can be prepared by coating.

Means for Solving the Problems

To achieve the above objects, the present inventors have designed and chemically synthesized novel compounds which are arylamine compounds having a molecular weight of from 1500 to 6000 and its derivative, experimentally prepared various organic EL devices using the compounds, and closely investigated characteristic evaluation of the devices, thereby leading to completion of the present invention.

That is, the above objects of the present invention have been achieved by providing an arylamine compound having a molecular weight of from 1500 to 6000 represented by the general formula (1), and an organic electroluminescence device comprising a pair of electrodes, and at least one organic layer interposed therebetween, wherein the device contains the compound as a constituent material of the at least one organic layer:

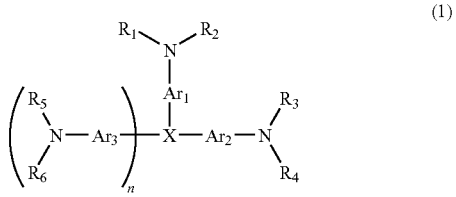

wherein X represents a single bond, CH, $CH_2$, N or NH; $Ar_1$, $Ar_2$ and $Ar_3$ represent a phenyl group, a biphenyl group or a terphenyl group; $R_1$, $R_2$, $R_3$, $R_4$, $R_5$ and $R_6$ each independently represent an aryl group, wherein the aryl group may be substituted with a diarylamino group so as to form a triphenylamine moiety structure, and further the terminal aryl groups may be substituted with a diarylamono structure group-containing group so as to form a triphenylamine-like moiety structure repeatedly; n is 0 or 1.

Preferred compounds among the arylamine compounds having a molecular weight of from 1500 to 6000 represented by the general formula (1) of the present invention are those having 9 or 10 nitrogen atoms in their molecules, and particularly preferred compounds are those having 10 nitrogen atoms. Further, Preferred compounds among the arylamine compounds having a molecular weight of from 1500 to 6000 represented by the general formula (1) are those having 7 to 9 triphenylamine-like moiety structures in their molecules.

As specific examples of the groups $R_1$ to $R_6$ in the general formula (1), a substituted or unsubstituted phenyl group, a substituted or unsubstituted biphenyl group, a substituted or unsubstituted naphthyl group, and a substituted or unsubstituted terphenyl group are exemplified.

The arylamine compound having a molecular weight of from 1500 to 6000 represented by the general formula (1) of the present invention not only has excellent hole injecting and transporting characteristics, but can easily form a stable thin film by coating. As a result, it was clarified that an organic EL device of high efficiency and high durability can be realized.

The organic EL device of the present invention has excellent hole injecting and transporting characteristics, and can realize high efficiency and high durability due to use of an arylamine compound having a molecular weight of from 1500 to 6000 that forms a stable thin film.

ADVANTAGE OF THE INVENTION

The present invention relates to an arylamine compound having a molecular weight of from 1500 to 6000, which is useful as a material of a thin film of a hole injecting layer or a hole transporting layer of an organic EL device, and relates to an organic EL device prepared using the compound. By the present invention, emission efficiency and durability of the conventional coating type organic EL device can remarkably be improved.

BEST MODE FOR CARRYING OUT THE INVENTION

Figure 1:
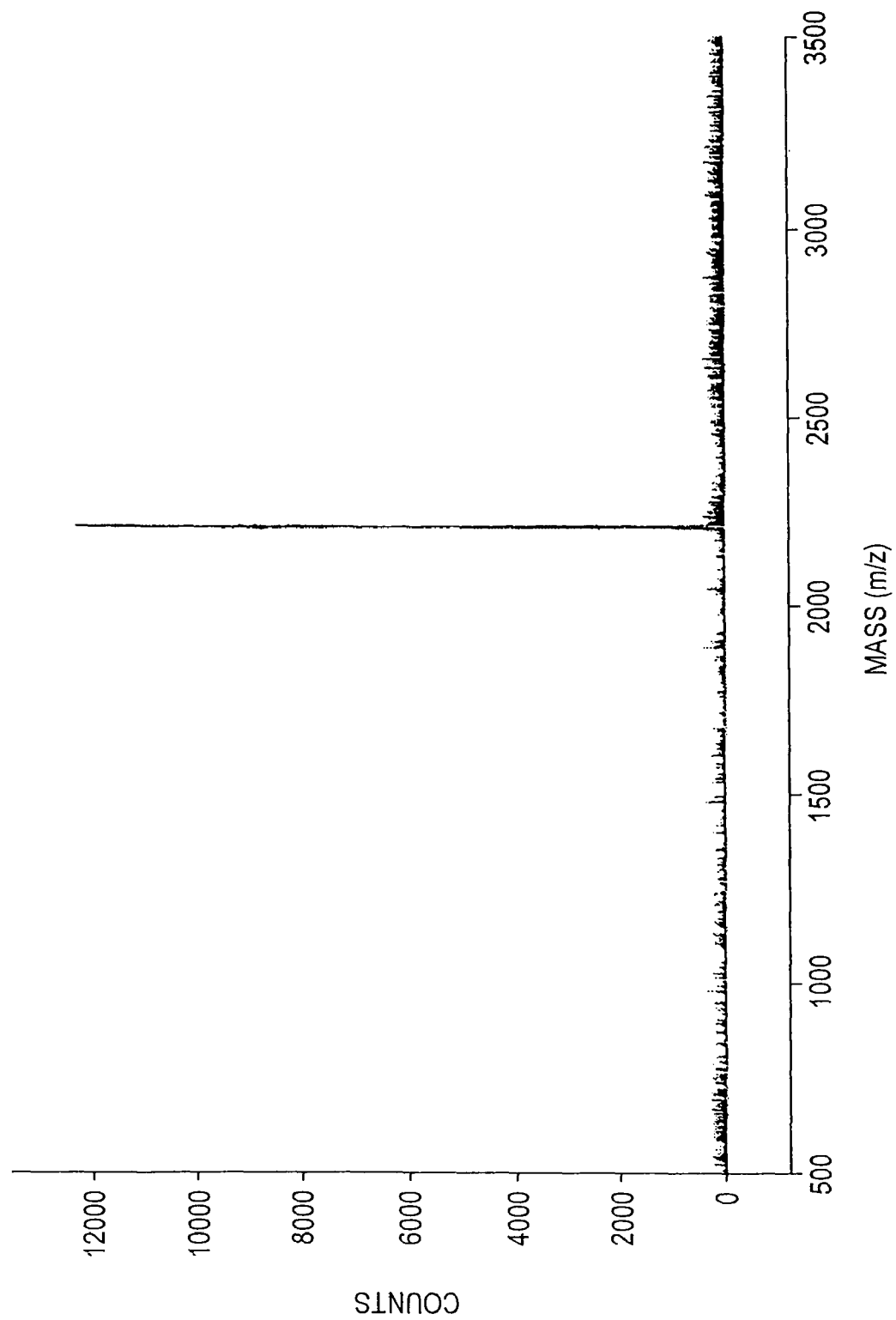
FIG. 1 is a chart of TOF-MS.

The molecular weight of the arylamine compound and its derivative of the present invention is preferably from 1500 to 6000. The reasons that the lower limit of the molecular weight is thus defined in the present invention are that when the molecular weight is smaller than 1500, a stable thin film cannot be formed by coating, and defect such as crystallization occurs when driving the organic EL device prepared. On the other hand, the reason that the molecular weight is 6000 or less is that compounds having different molecular weight by-produce, and it is difficult to separate such compounds.

The arylamine compound having a molecular weight of from 1500 to 6000 of the present invention can be synthesized by condensing an arylamine and an allyl halide through Ullmann reaction or the like.

Of the arylamine represented by the general formula (1), examples of preferred compound are shown below, but the present invention is not limited to those compounds.

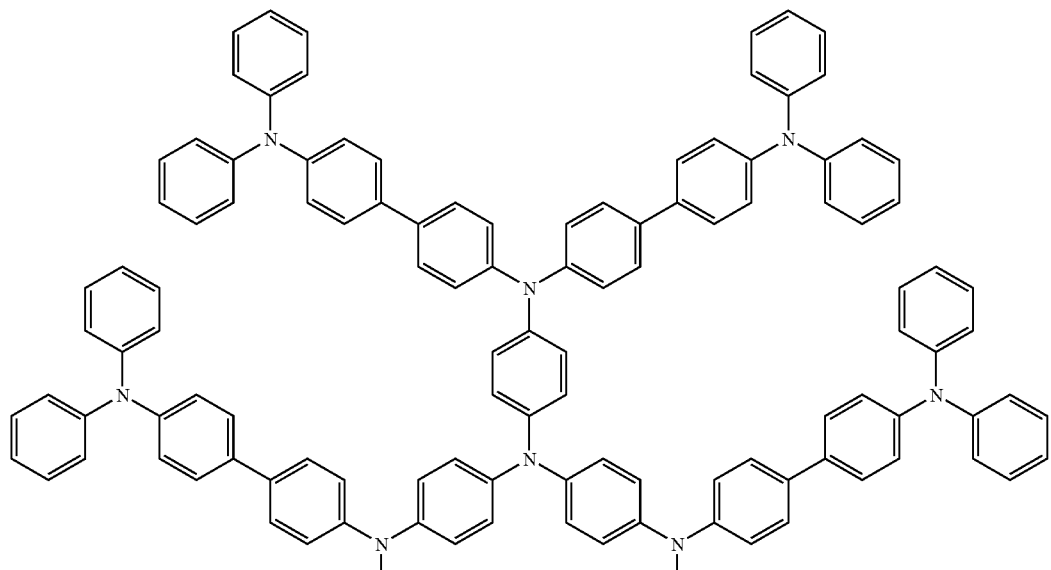
(2)
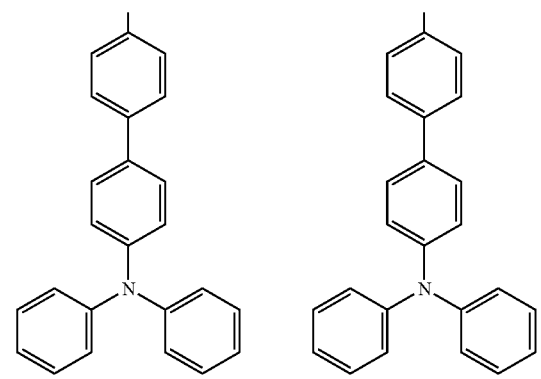
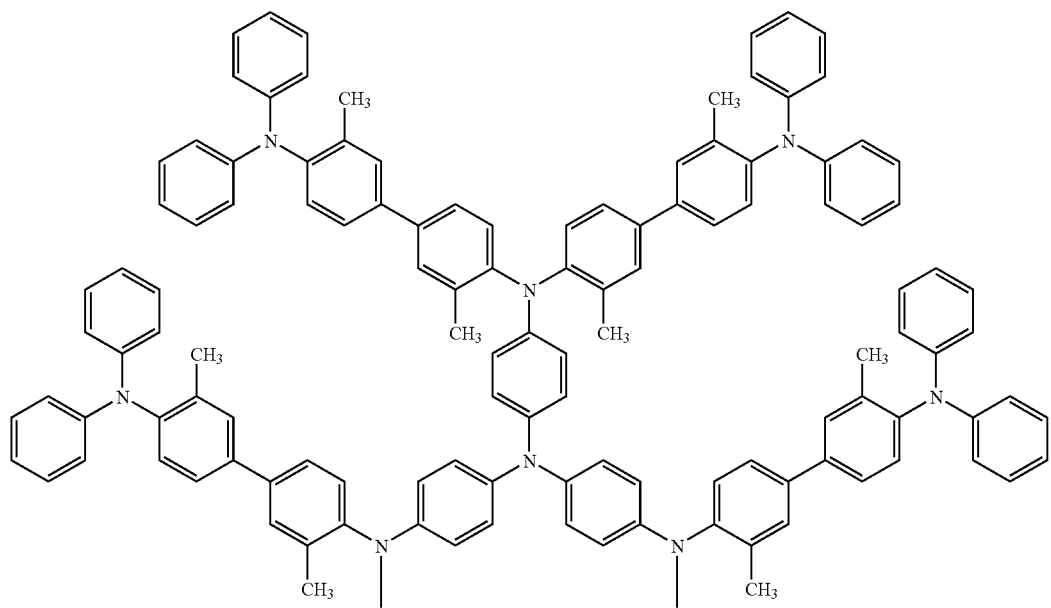
(3)

-continued
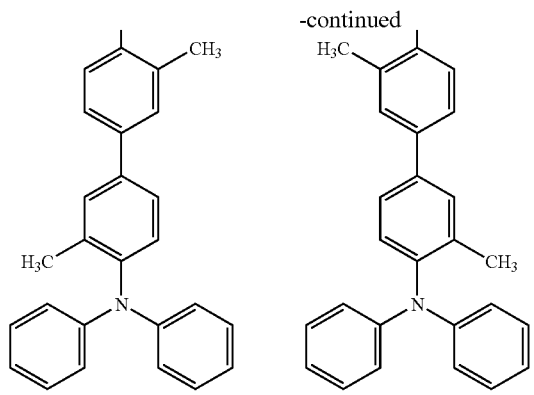
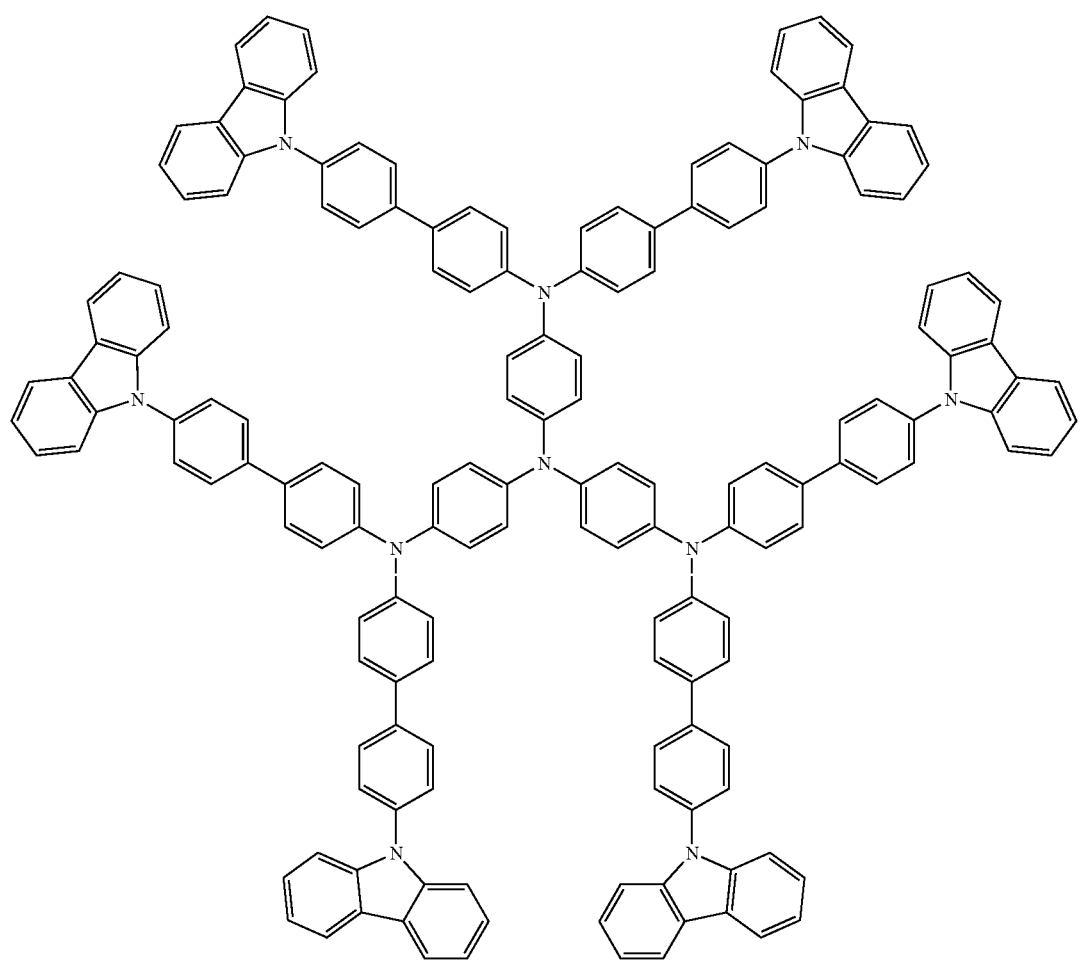
(4)

-continued
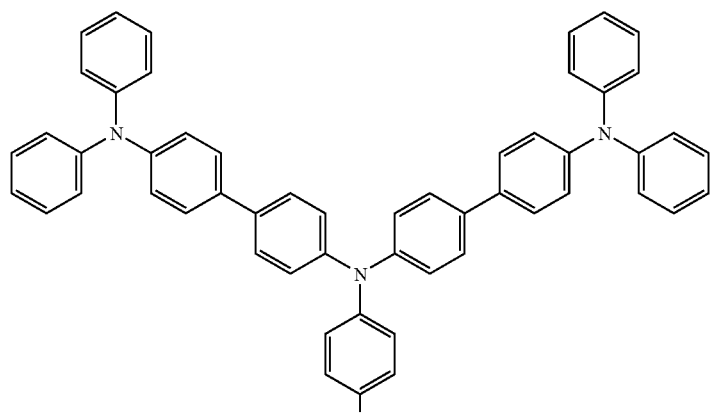
(5)
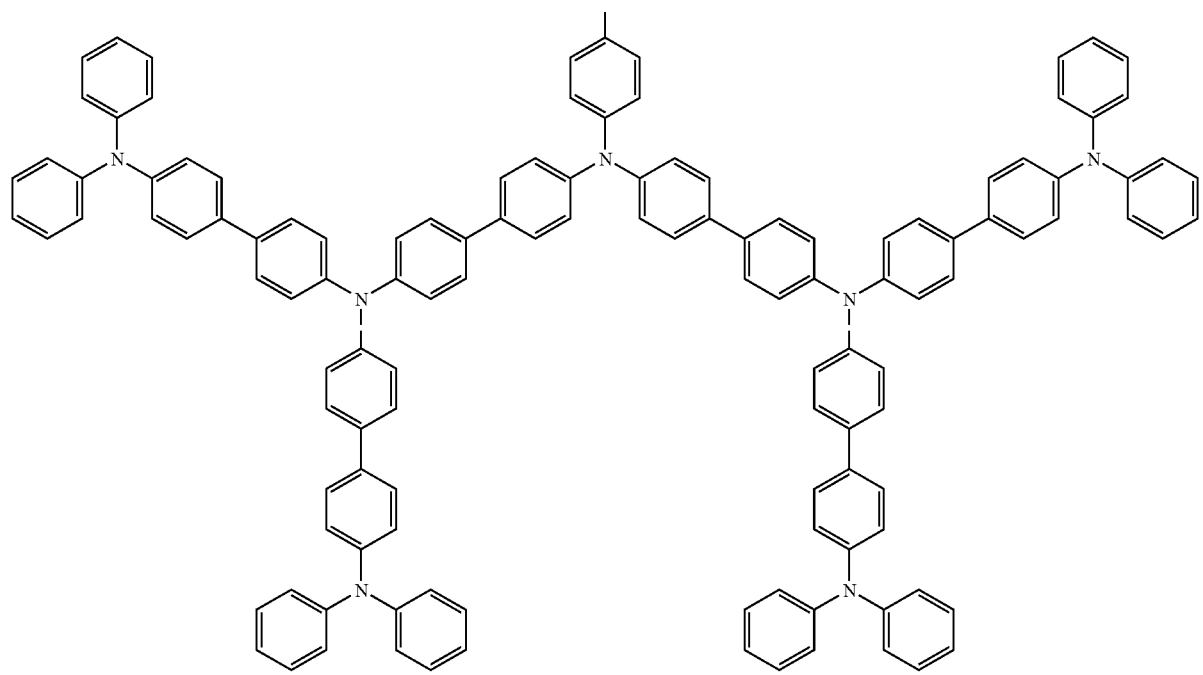
(6)
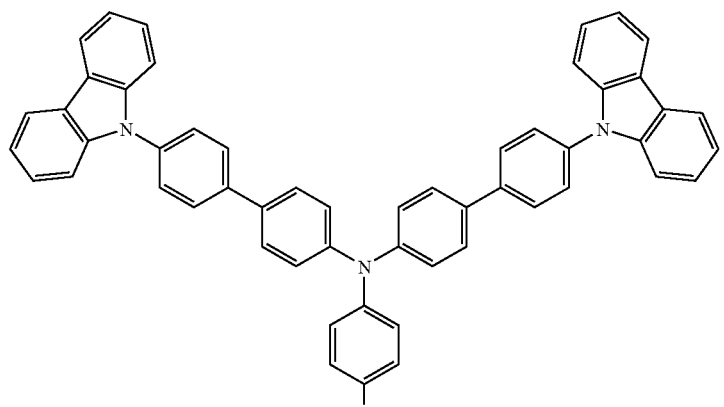

-continued
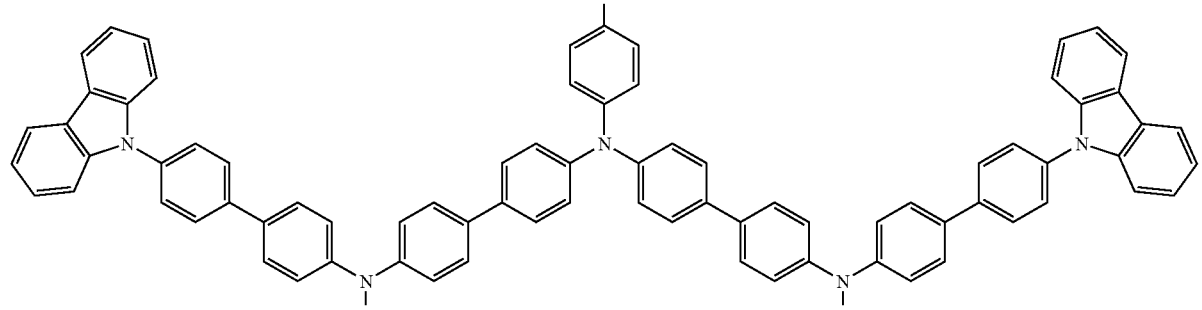
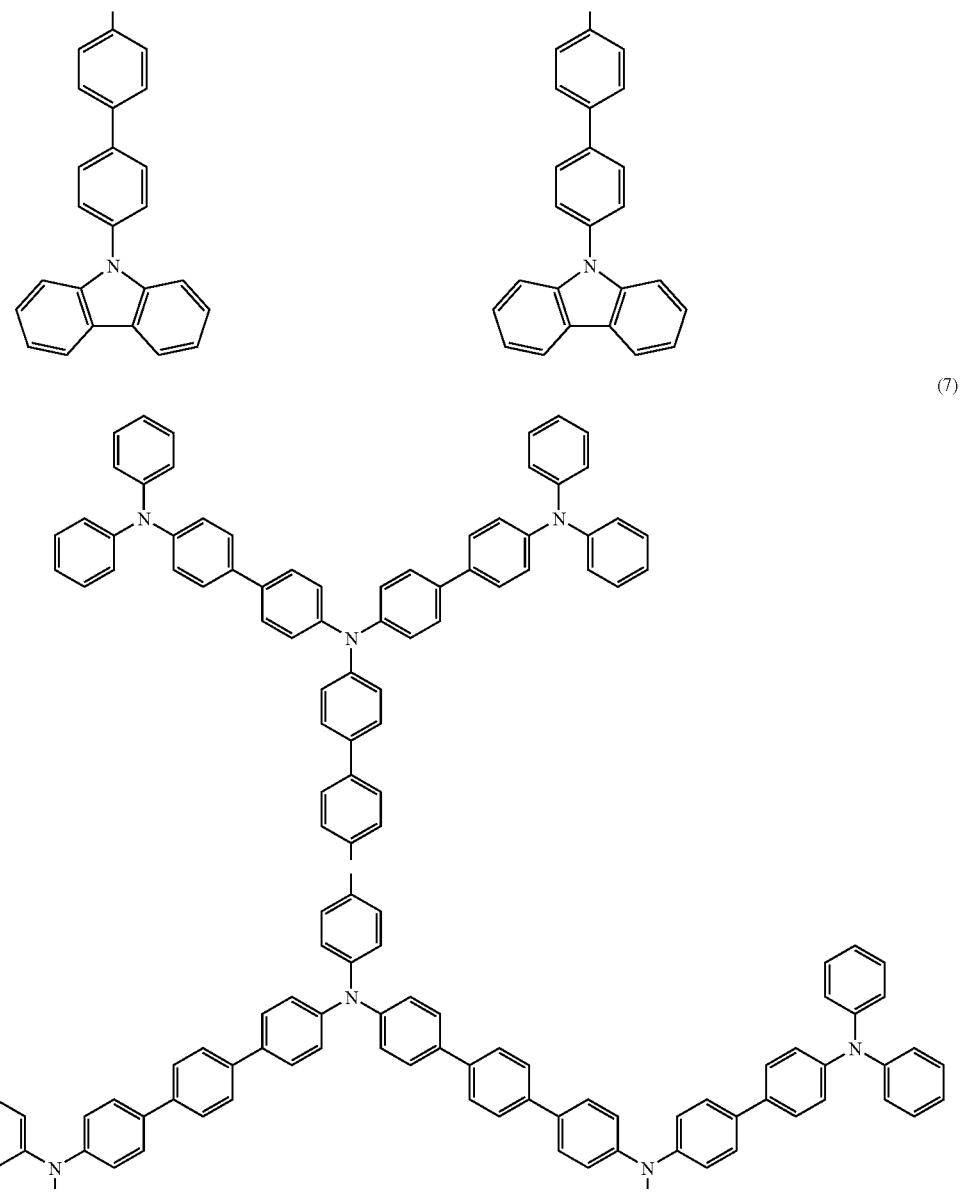
(7)

-continued
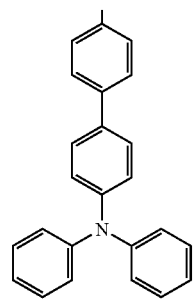
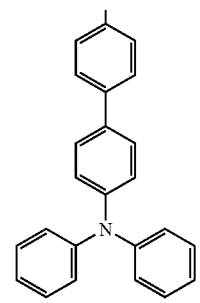
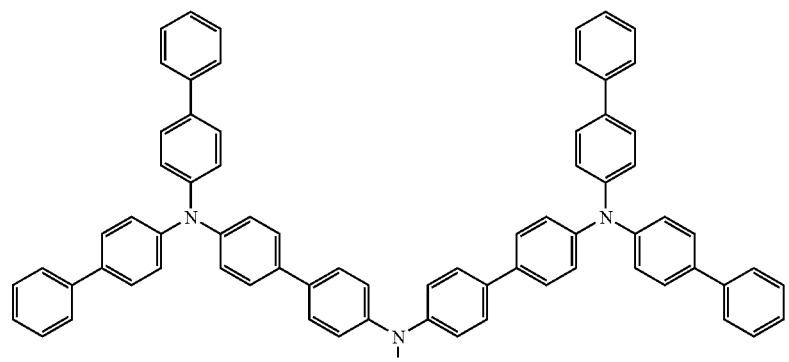
(8)
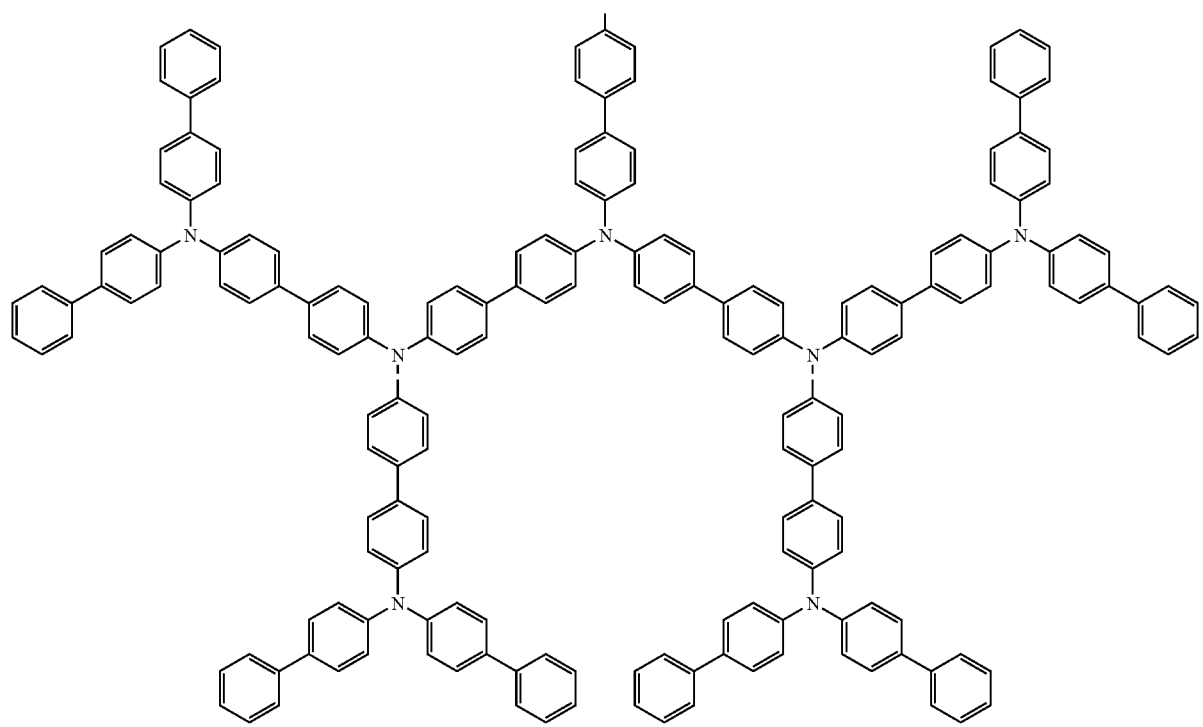

(9)
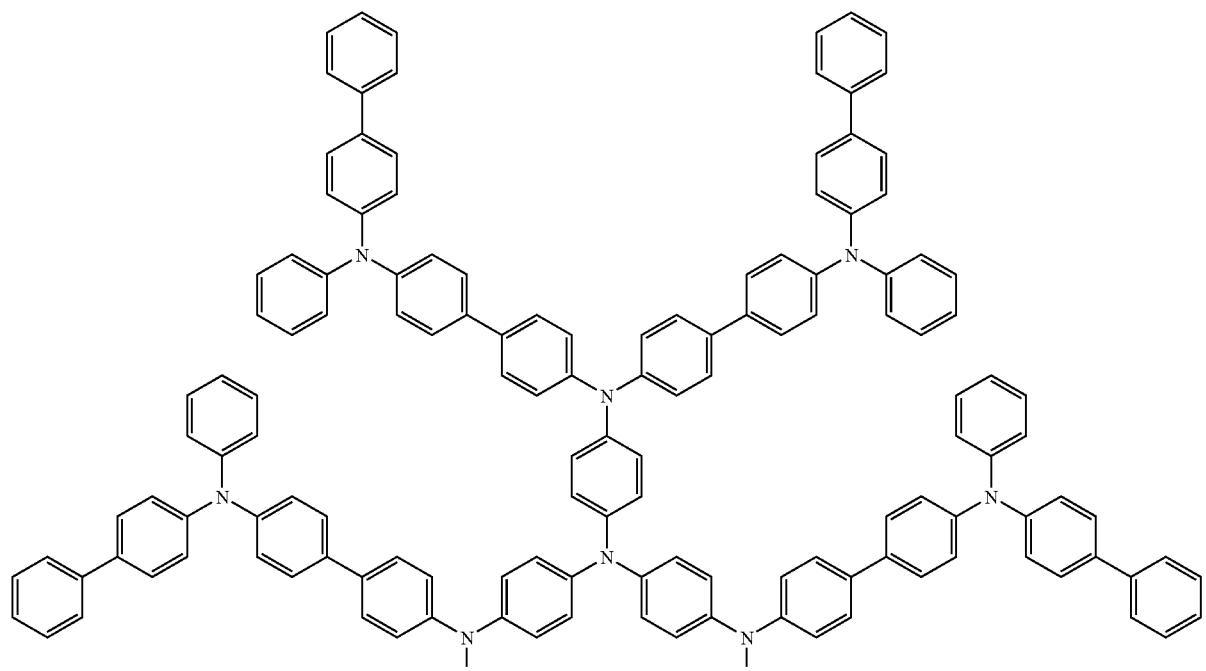
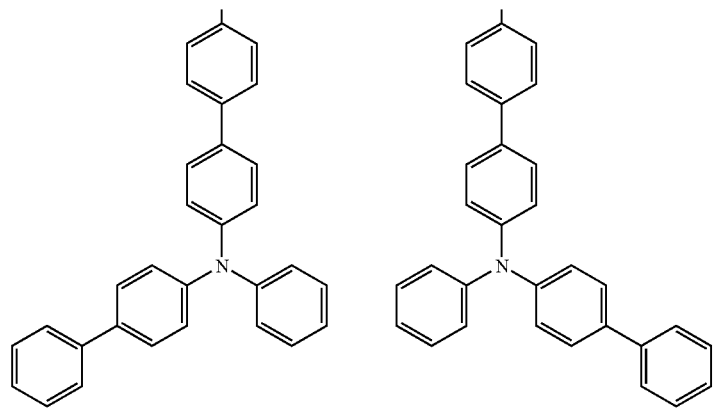
(10)
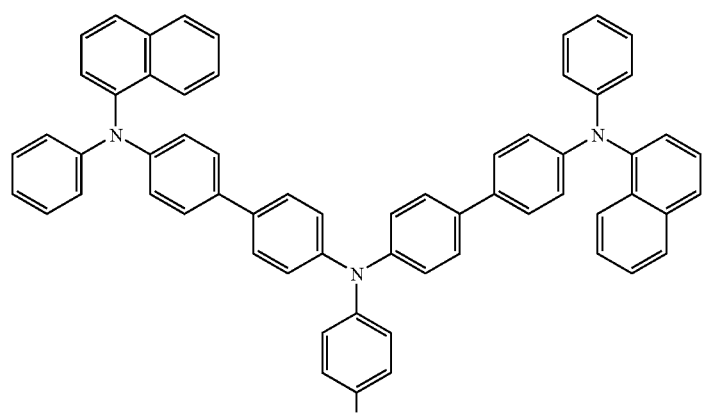

-continued
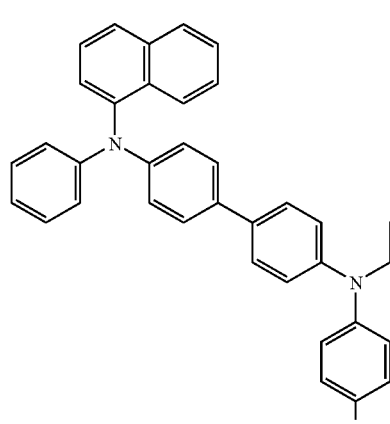
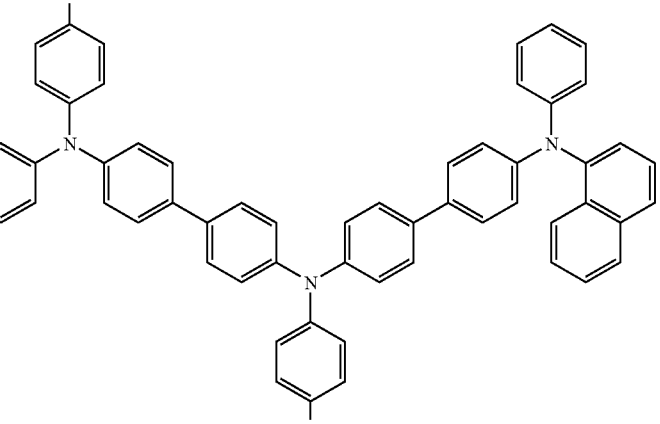
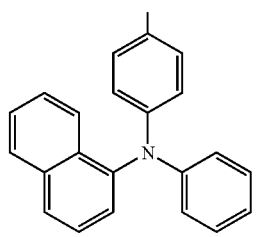
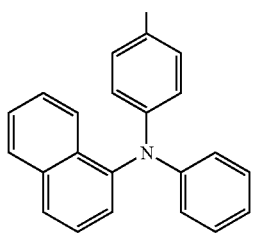
(11)
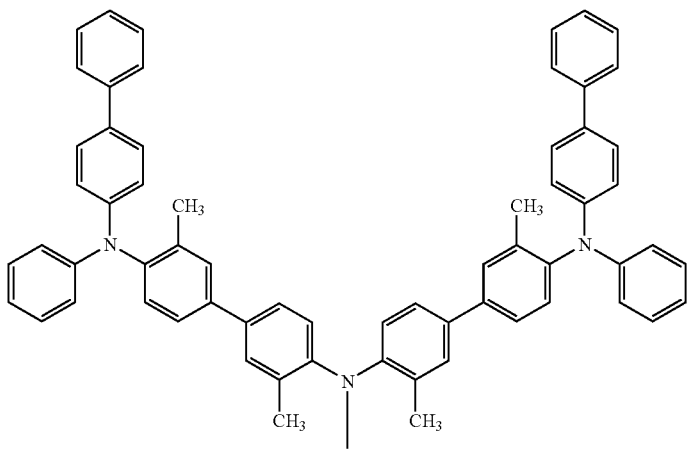
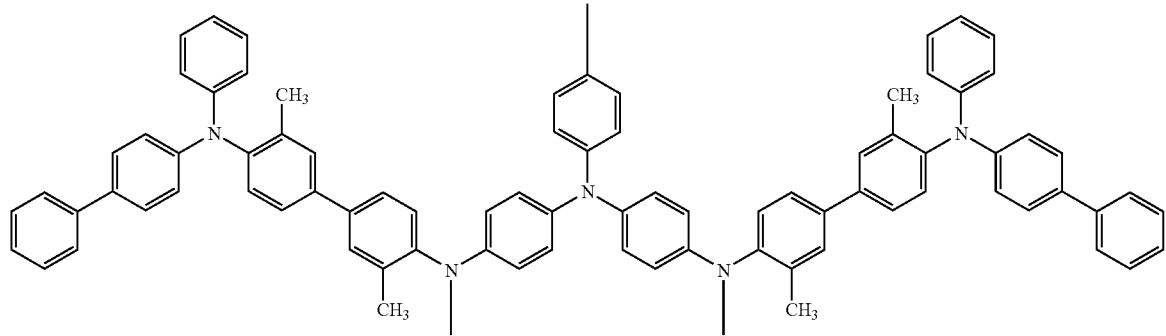

-continued
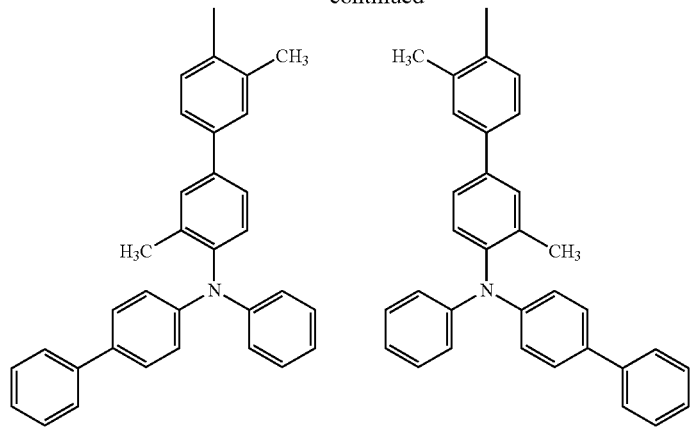
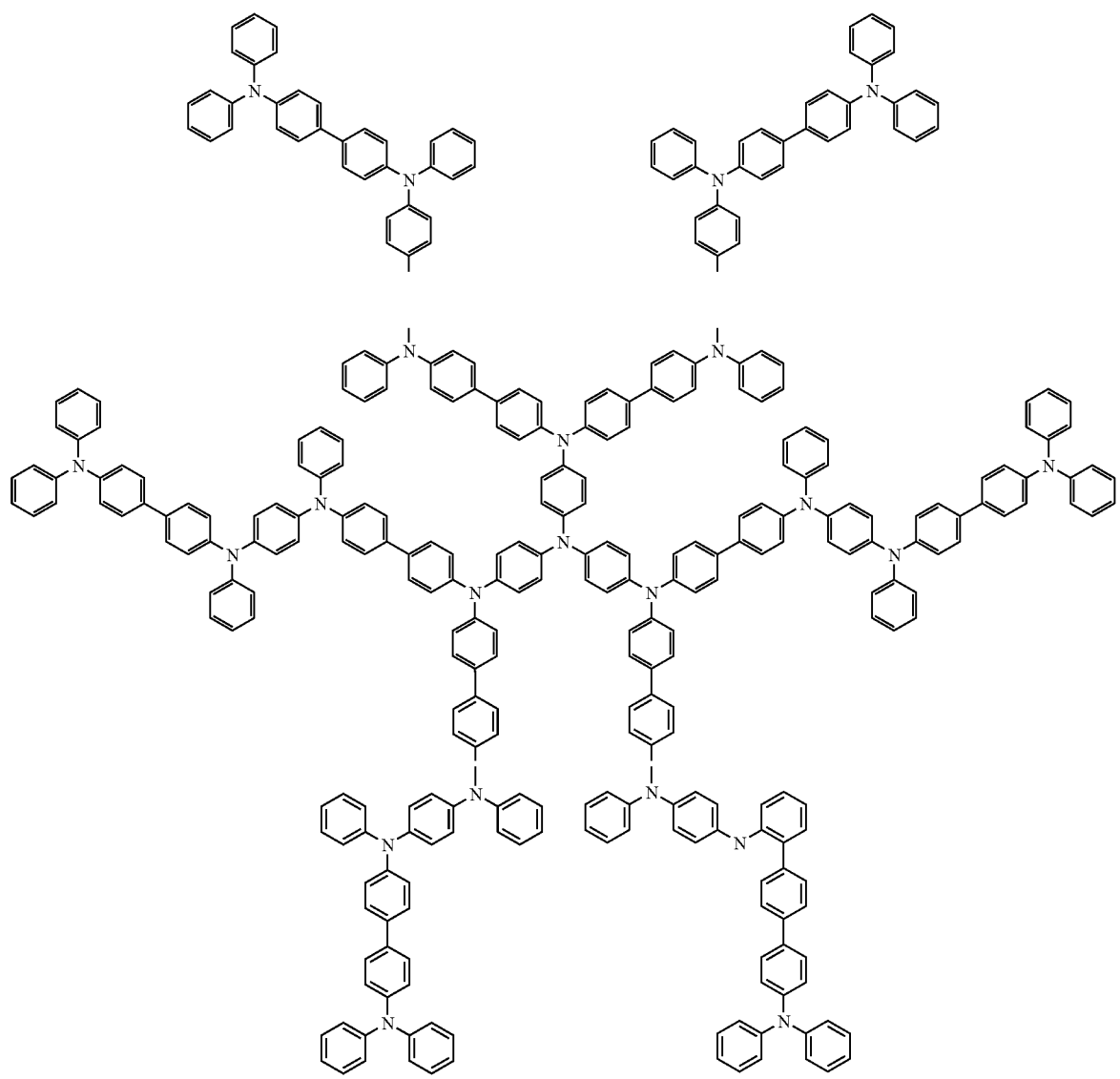
(12)

-continued

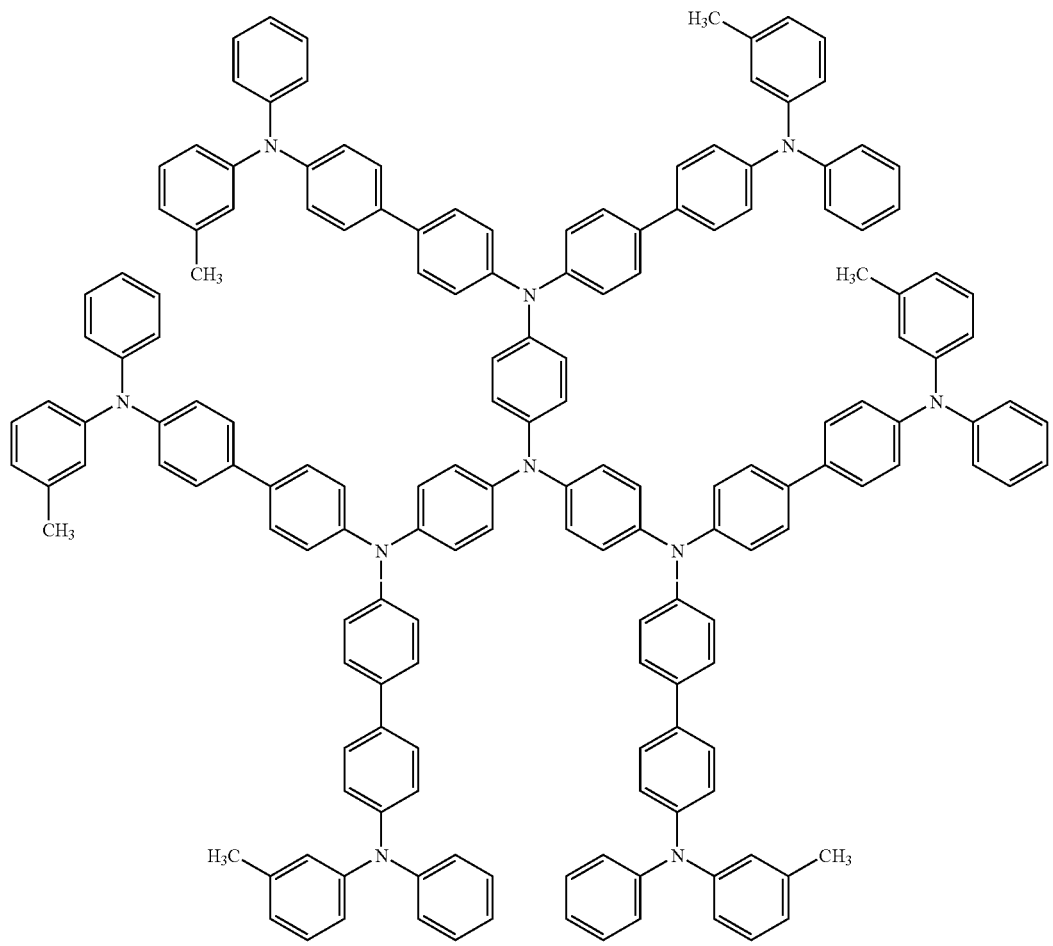

(13)

As shown in the above exemplified compounds, the "diarylamino structure-containing group" includes 4-(diarylamino)phenyl group, and a group having a substituent on a part of a phenyl or phenylene group constituting 4-(diarylamino)phenyl group. In the present specification, the "triphenylamine-like moiety structure" includes a triphenylamine structure having a substituent and the terminal group that the compound of the above formula (4) or (6) has, as well as an unsubstituted triphenylamine structure.

Purification of the compound of the present invention was conducted by purification with column chromatography, recrystallization or crystallization with a solvent, and the like. The compound could be purified up to a single molecular species by column purification or the like. Structure of the compound was identified with an elementary analysis or the like. One of the characteristics that the compound of present invention possesses is that regardless of a large molecular weight, the compound is not a mixture of various molecular species like a polymer material, but is constituted of a single molecular species.

The present inventors used a time-of-flight mass spectrometer (hereinafter referred to as TOF-MS) with which a compound is ionized, and drifted in a potential difference space to detect, as means for demonstrating to be a single molecular species. The analytical result using TOF-MS demonstrates homogeneity of the compound used in the present invention.

Because of being a single molecular species of high purity, carrier trap due to impurities, which is a factor of durability deterioration of an organic EL device, is less, and it is suitable as an organic layer constituting an organic EL device.

As physical property values of the compound, DSC measurement (Tg) and melting point measurement were conducted. The melting point serves as a measure of deposition property, and the glass transition point (Tg) serves as a measure of stability in a thin film state. The melting point and glass transition point were measured using a powder with a differential scanning calorimeter, a product of MacScience.

Further, work function was measured by preparing a 100 nm thin film on an ITO substrate and using an atmospheric photoelectron spectrometer AC2, a product of Riken Keiki Co., Ltd. The work function serves as a measure of hole injecting ability.

With the compound of the present invention, a coating liquid can be prepared, and an organic EL device can be prepared by forming a thin film by coating. For a solvent used to prepare the coating liquid, a solvent such as cyclohexane, THF, trichloroethane or o-dichlorobenzene is suitable. To the coating liquid, a functional compound such as a luminescent material or an electron transporting material can be mixed.

As a film-forming method using the coating liquid, coating methods such as a spin coating method, a casting method, a microgravure method, a gravure coating method, a bar coating method, a roll coating method, a wire bar coating method, a dip coating method, a spray coating method, a screen printing method, a flexo printing method, an off-set printing method, and an ink-jet printing method can be used.

Thickness of the coating film can be selected such that driving voltage and durability of the organic EL device are optimal. Such a thickness that at least pinholes do not generate is necessary. When the thickness is too thick, driving voltage of the organic EL device increases, which is not preferred. Therefore, the thickness of the coating film is, for example, from 1 nm to 1 µm, and preferably from 10 to 200 nm.

The structure of the organic EL device of the present invention includes a structure comprising, successively on a substrate, an anode, a hole injecting layer, a hole transporting layer, a layer serving as both emission layer and electron transporting layer, a hole blocking layer and a cathode, or a structure comprising, successively on a substrate, an anode, a hole injecting layer, a hole transporting layer, an emission layer, a hole blocking layer, an electron transporting layer, an electron injecting layer and a cathode. In those multilayered structures, by combining functions of several organic layers, such as a structure comprising an anode, a layer serving as all of hole injecting layer/hole transporting layer/emission layer/electron transporting layer, a hole blocking layer and a cathode, the number of the organic layers can be reduced. Further, the organic EL device of the present invention may have a new functional layer other than the above.

As the anode of the present invention, an electrode material having large wok function, such as ITO, NESA or tin oxide, is used. As the hole injecting layer, a coating film of the arylamine compound of the present invention or a high molecular weight material is used. By depositing a low molecular weight material on the coating film or laminating a high molecular weight material thereon, a hole transporting layer, an emission layer and the like can be laminated. As the examples of the high molecular weight material, PEDOT/PSS, a polymerizable polymer having a hole transporting aromatic amine at a side chain or in a main chain, and the like are exemplified.

Further, a material such as copper phthalocyanine (hereinafter referred to as CuPc), starburst type triphenylamine derivatives and naphthalene amine compounds, can be used through deposition.

As the hole transporting layer, as well as the arylamine compound of the present invention, benzidine derivatives such as N,N'-diphenyl-N,N'-di(m-tolyl)benzidine (hereinafter referred to as TPD) and N,N'-diphenyl-N,N'-di(α-naphthyl)benzidine (hereinafter referred to as NPD), and dimmer, trimer and tetramer of various triphenylamines can be used.

As the emission layer or electron transporting layer of the present invention, a mixture of the arylamine compound of the present invention and a luminescent material or an electron transporting material, or a mixture of a high molecular weight material and an electron transporting material can be used. As the examples of the high molecular weight material, polydialkylfluorene derivatives, poly(N-vinylcarbazole) (hereinafter referred to as PVK), polyaniline, polythiophene, poly(p-phenylenevinylene), polysiloxane, and the like are exemplified. Further, electron transporting materials such as various luminescent materials, carbazole derivatives, aluminum complexes of quinoline, oxazole derivatives, and the like can be used.

Further, by adding a luminescent material called a dopant, including a fluorescent dye such as quinacridone, coumarin 6 or rubrene, or a phosphorescent material such as an iridium complex of phenylpyridine; or an electron transporting material such as oxazole derivatives or triazole derivatives, to the emission layer, the performance of the organic EL device of the present invention can be improved.

The organic EL device of the present invention may have a hole blocking layer or an electron injecting layer. As the hole blocking layer, bathocu-proine, oxazole derivatives and the like can be used. As the electron injecting layer, lithium fluoride and the like can be used. As the cathode of the present invention, an electrode material having small work function, including metals such as magnesium, calcium or aluminum, and alloys of at least one of those metals with silver, indium or the like is used.

EXAMPLES

The embodiment of the present invention is specifically described below by the Examples, but the invention is not limited to the following Examples so long as not exceeding its gist.

Example 1

Synthesis of 4,4',4"-tris[N,N-bis(4'-diphenylaminobiphenyl-4-yl)]triphenylamine (Hereinafter Referred to as TPA-9) (2))

12.4 g of acetamide, 45.0 g of 4-iodo-4'-diphenylaminobiphenyl, 20.9 of potassium carbonate, 2.0 g of copper powder, 1.1 g of sodium hydrogensulfite and 15 ml of diphenyl ether were reacted at 210° C. for 10 hours under a nitrogen atmosphere while stirring. After completion of the reaction, 400 ml of toluene was added, followed by stirring for 1 hour. The mixture was heat filtered, and the filtrate was condensed to obtain crude crystals of an acetylated form. 220 ml of isopropyl alcohol and 11.8 g of potassium carbonate were added to the crude crystals, followed by refluxing for 7 hours. The reaction liquid was condensed to obtain a crude product of a deacetylated form. The dried crude product was purified by column chromatography to obtain 11.6 g of a white powder of N,N-bis(4'-diphenylaminophenyl-4-yl)amine.

1.00 g of N,N-bis(4'-diphenylaminophenyl-4-yl)amine, 0.23 g of tris(4-bromophenyl)amine, 0.26 g of sodium tertiary butoxide, 0.02 g of palladium (II) acetate and 0.003 g of sodium hydrogensulfite were added to 7 ml of dehydrated toluene, followed by heating, and under reflux, a solution of tri tertiary butyl phosphine dissolved in 3 ml of dehydrated toluene was added to react for 4 hours.

After completion of the reaction, 60 ml of toluene was added, followed by stirring for 1 hour. The mixture was heat filtered. After allowing to stand to cool, precipitates in the filtrate were again filtered to obtain a crude product. The dried crude product was purified with column chromatography (carrier: silica gel, eluting solution: chloroform/hexane=5/3) to obtain 0.33 g (yield 31%) of TPA-9.

After the purification, chemical structure of the white powder obtained was identified with an elementary analysis. The results of the elementary analysis were as follows.

Theoretical value (carbon 88.17%) (hydrogen 5.94%) (nitrogen 6.35%)

Found value (carbon 87.85%) (hydrogen 5.98%) (nitrogen 6.17%)

Figure 2:
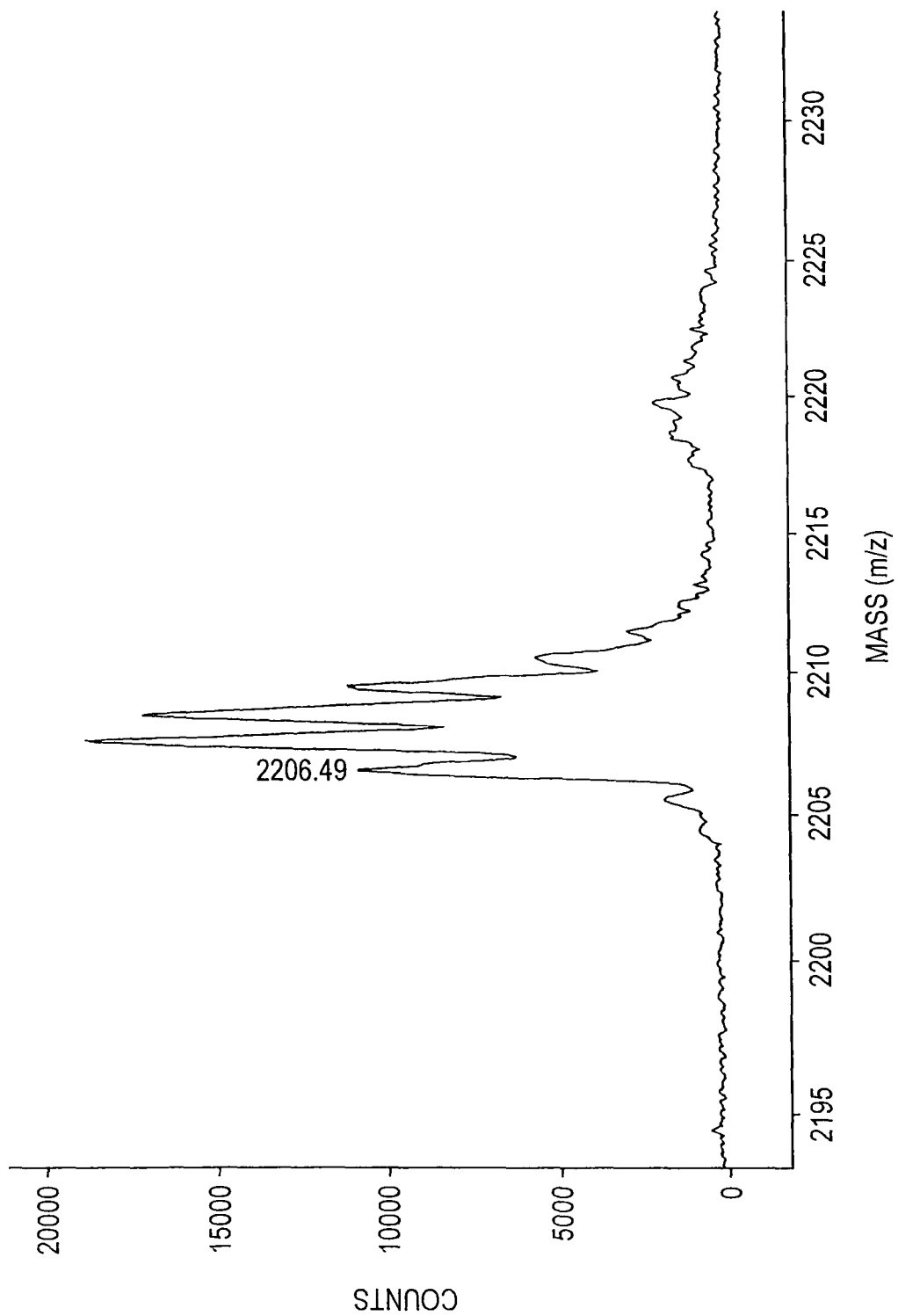
FIG. 2 is an enlarged chart of TOF-MS.

The identified compound was analyzed using MALDI-TOF-MS (Perspective Biosystem Inc., Shinshu University, Faculty of Textile Science & Technology, Department of Functional Polymer Science) which is a mass analyzer. The measurement results of TOF-MS were shown in FIG. 1, and its enlarged view was shown in FIG. 2.

From the results of TOF-MS, it was confirmed that TPA-9 is isotopes having a single chemical structure, that have molecular weights of 2206, 2207, 2205, 2208, 2210 and the like. From the above result, it is apparent that regardless of having high molecular weight of 1500 or higher, the compound of the present invention has high purity and is homogeneous.

Example 2

(Synthesis of 4,4',4''-tris[N,N-bis(4'-diphenylamino-3,3'-dimethylbiphenyl-4-yl)]triphenylamine (Hereinafter Referred to as DM-TPA-9) (3))

10 g of N,N-bis(4'-diphenylamino-3,3'-dimethyl-biphenyl-4-yl)amine, 2.18 g of tris(4-bromophenyl)amine, 2.6 g of tertiary butoxysodium and 0.015 g of palladium (II) acetate were added to 150 ml of dehydrated toluene, followed by heating at 60° C., and 0.055 g of tri tertiary butyl phosphine was added to react at 95° C. for 11 hours.

After completion of the reaction, 100 ml of toluene was added, followed by stirring for 1 hour. The mixture was allowed to stand to cool to 45° C., and heat filtered. The filtrate was condensed to obtain 19 g of a crude product. The dried crude product was purified with column chromatography (carrier: silica gel, eluting solution: chloroform/hexane=1/1) to obtain 3.53 g (yield 32%, melting point 220.0-222.5° C.) of DM-TPA-9.

Example 3

(Synthesis of 4,4',4''-tris{N,N-bis[4'-(carbazol-9-yl)-biphenyl-4-yl]amino}triphenylamine (Hereinafter Referred to as CZ-TPA-9) (4))

10 g of N,N-bis[4'-(carbazol-9-yl)biphenyl-4-yl)]amine, 2.4 g of tris(4-bromophenyl)amine, 2.85 g of tertiary butoxysodium and 0.017 g of palladium (II) acetate were added to 200 ml of dehydrated toluene, followed by heating at 60° C., and 0.06 g of tri tertiary butyl phosphine was added to react at 95° C. for 12 hours.

After completion of the reaction, 100 ml of toluene was added, followed by stirring for 1 hour. The mixture was allowed to stand to cool to 45° C., and heat filtered. The filtrate was condensed to obtain 33 g of a crude product. The dried crude product was introduced in 200 ml of toluene, followed by reflux stirring for 1 hour and then filtration. The residue was dissolved in 200 ml of THF, and insoluble content was removed by filtration. The filtrate was added dropwise to 300 ml of methanol to precipitate crystals, and 2.55 g (yield 24%, melting point 249.5-252.0° C.) of CZ-TPA-9 was obtained.

Example 4

(Synthesis of 1', (1')', (1')''-tris[N,N-bis(4'-diphenylamino-biphenyl-4-yl)amino]-tris-4,4'-biphenylamine (Hereinafter Referred to as BP-TPA-9) (5))

3.6 g of N,N-bis(4'-diphenylaminobiphenyl-4-yl)-4-bromoaniline, 0.5 g of triphenylamine-4,4',4''-boric acid and 2.6 ml of 2M sodium carbonate were added to 50 ml of dehydrated toluene, and 0.023 g of tetrakis(triphenylphosphine) palladium (0) was added under a nitrogen stream to react at 85° C. for 96 hours.

After completion of the reaction, 100 ml of toluene was added, and the mixture was stirred at 80° C. for 1 hour, and then allowed to stand to cool to 45° C. The reaction liquid was transferred to a separatory funnel. A toluene layer was washed with water, and transferred to an eggplant flask. A solvent was condensed 30 ml to precipitate crystals. The crystals were filtered off, and the resulting crude product was dissolved in 30 ml of THF. 60 ml of toluene was added dropwise at room temperature to precipitate crystals, thereby obtaining 0.42 g (yield 12.7%, melting point 222.0-225.0° C.).

A white powder purified by repeating crystallization further two times was subjected to an elemental analysis to identify the chemical structure. The results of the elementary analysis were as follows.

Theoretical value (carbon 88.78) (hydrogen 5.46%) (nitrogen 5.75%)

Found value (carbon 89.09%) (hydrogen 5.74%) (nitrogen 5.68%)

Example 5

Regarding the compound of the present invention and MTDATA, a glass transition point was obtained by a differential scanning calorimeter (a product of MacScience). The measurement results were as follows, and it was confirmed that the compound of the present invention has remarkably high glass transition point.

| | |
|---|---|
| TPA-9 | Glass transition point: 188° C. |
| DM-TPA-9 | Glass transition point: 173° C. |
| CZ-TPA-9 | Glass transition point: 221° C. |
| BP-TPA-9 | Glass transition point: 204° C. |
| MTDATA | Glass transition point: 76° C. |

Example 6

TPA-9 (2) of the present invention was dissolved in 1,1,2-trichloroethane in a concentration of 2 mass %, and the resulting coating liquid was applied to an ITO substrate by a spin coating method, and dried in a vacuum oven at 100° C. to form a hole injecting layer of about 20 nm. It was observed by a polarizing microscope observation that the compound of the synthesis example of the present invention forms a thin film that is homogeneous, and does not have a defect.

Example 7

Regarding thin films of the compounds of the present invention, prepared by coating, work function was measured with an atmospheric photoelectron spectrometer (a product. of Riken Keiki Co., Ltd., AC2). The measurement results are shown below.

| | |
|---|---|
| TPA-9 | Work function: 5.06 eV |
| DM-TPA-9 | Work function: 5.07 eV |
| CZ-TPA-9 | Work function: 5.26 eV |
| BP-TPA-9 | Work function: 5.21 eV |

From the above results, it can be considered that the thin film prepared using the compound used in the organic EL device of the present invention has an energy level appropriate as a hole injecting and transporting layer.

Example 8

Figure 3:
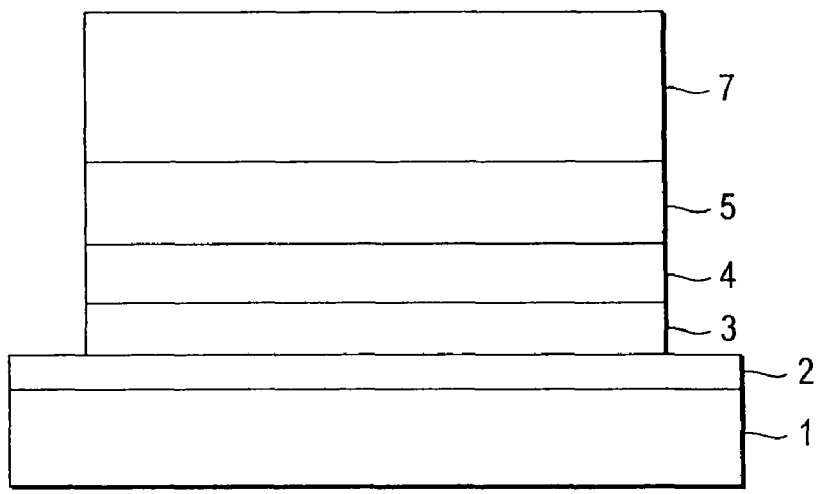
FIG. 3 is a view showing the EL device structure of Example 8.

An organic EL device was prepared by successively laminating a hole injecting layer 3, a hole transporting layer 4, a layer serving as both emission layer and electron transporting layer 5 and a cathode (aluminum magnesium electrode) 7, on an ITO electrode previously formed as a transparent anode 2 on a glass substrate 1, as shown in FIG. 3.

The glass substrate 1 having ITO of 150 nm film thickness formed thereon was washed with an organic solvent, and then subjected to an oxygen plasma treatment to clean the surface.

A coating liquid of TPA-9 (2) dissolved in 1,1,2-trichloroethane was applied to the ITO substrate by a spin coating method, and dried in a vacuum oven at 100° C. to form the hole injecting layer 3 of about 20 nm thickness. This was fitted in a vacuum deposition apparatus, and pressure was reduced to 0.001 Pa or lower.

Subsequently, as the hole transporting layer 4, TPD was formed in about 30 nm at a deposition rate of 0.6 Å/s. Next, as the layer serving as both emission layer and electron transporting layer 5, Alq was formed in about 50 nm at a deposition rate of 0.6 Å/s. The above depositions each were continuously conducted without breaking vacuum. Finally, a mask for cathode deposition was inserted, and an alloy of MgAg was deposited in about 200 nm at a ratio of 10:1 to form the cathode 7. The device prepared was stored in a vacuum desiccator, and characteristic measurement was conducted at ordinary temperature in the atmosphere.

Characteristics of the organic EL device of the present invention thus formed were evaluated by emission luminance in the case of loading a current density of 400 mA/cm$^2$, emission efficiency defined by emission luminance/voltage, and the maximum luminance before breakthrough when increasing current density load. The maximum luminance measured by this method reflects electrical stability of a device, and is therefore a measure of durability of the organic EL device.

When current density of 400 mA/cm$^2$ was loaded to the organic EL device, a stable green emission of 25000 cd/m$^2$ was obtained. Emission efficiency at this luminance was high efficiency of 5.10 cd/A. Device voltage at this time was 14.0 V. when load was further increased, the maximum luminance showed 21000 cd/m$^2$, and the device deteriorated.

Comparative Example 1

For the sake of comparison, the material of the hole injecting layer 3 was replaced with MTDATA, and its characteristic was examined. Because MTDATA could not prepare a thin film which is homogeneous and does not have defect, by coating, a thin film was prepared by deposition. That is, an ITO substrate was fitted in a vacuum deposition apparatus, pressure was reduced to 0.001 Pa or lower, and as the hole injecting layer 3, MTDATA was formed in about 20 nm at a deposition rate of 0.6 Å/s. Subsequently, similar to Example 5, the hole transporting layer, the layer serving as both emission layer and electron transporting layer, and the cathode were all formed by deposition. The above depositions each were continuously conducted without breaking vacuum.

When current density of 400 mA/cm$^2$ was loaded to the organic EL device using MTDATA, a stable green emission of 15300 cd/m$^2$ was obtained. Emission efficiency at this luminance was 3.90 cd/A. Device voltage at this time was 14.8 V. When load was further increased, the maximum luminance showed 16000 cd/m$^2$, and the device deteriorated.

Comparative Example 2

For further sake of comparison, the material of the hole injecting layer 3 was replaced with copper phthalocyanine, and its characteristic was examined. In place of MTDATA in Comparative Example 1, purified copper phthalocyanine was formed in about 20 nm at a deposition rate of 4 nm/min. Subsequently, similar to Comparative Example 1, a device was prepared.

When current density of 400 mA/cm$^2$ was loaded to the organic EL device using copper phthalocyanine, a stable green emission of 16200 cd/m$^2$ was obtained. Emission efficiency at this luminance was 4.12 cd/A. Device voltage at this time was 12.4 V. When load was further increased, the maximum luminance showed 18000 cd/m$^2$, and the device deteriorated.

From the above results, it is apparent that emission efficiency and durability of the organic EL device of the present invention are superior to the conventional EL device.

Example 9

Figure 4:
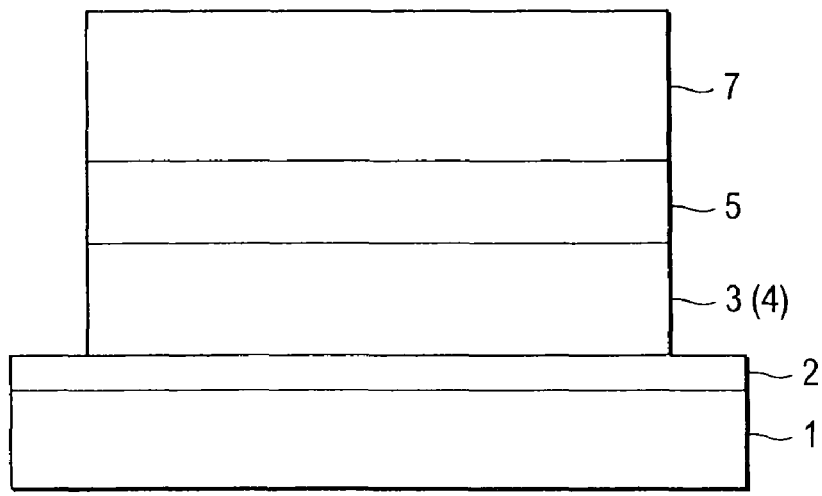
FIG. 4 is a view showing the EL device structure of Example 9.

An organic EL device was prepared by successively laminating a layer serving as both hole injecting layer and hole transporting layer 3 and 4, a layer serving as both emission layer and electron transporting layer 5 and a cathode (aluminum magnesium electrode) 7, on an ITO electrode previously formed as a transparent anode 2 on a glass substrate 1, as shown in FIG. 4. The glass substrate 1 having ITO of 150 nm film thickness formed thereon was washed with an organic solvent, and then subjected to an oxygen plasma treatment to clean the surface.

Similar to Example 8, TPA-9 (2) was applied to the ITO substrate by a spin coating method, and dried in a vacuum oven to form the layer serving as both hole injecting layer and hole transporting layer 3 and 4 of about 50 nm thickness. This was fitted in a vacuum deposition apparatus, and pressure was reduced to 0.001 Pa or lower. Next, as the layer serving as both emission layer and electron transporting layer 5, Alq was formed in about 50 nm at a deposition rate of 0.6 Å/s. Finally, a mask for cathode deposition was inserted, and an alloy of MgAg was deposited to form the cathode 7.

When current density of 400 mA/cm$^2$ was loaded to the organic EL device, a stable green emission of 8100 cd/m$^2$ was obtained.

Example 10

Figure 5:
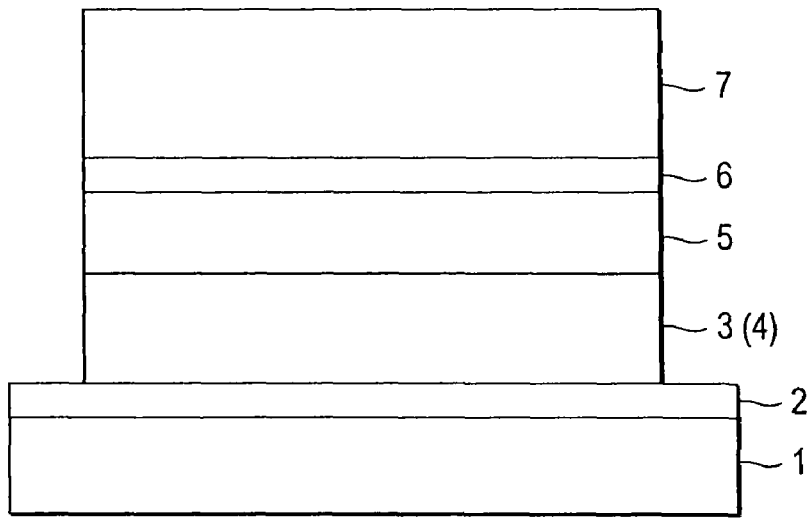
FIG. 5 is a view showing the EL device structure of Example 10.

A device in which a hole blocking layer was laminated between the layer serving as both emission layer and electron transporting layer 5 and the cathode (aluminum magnesium electrode) 7 was prepared, as shown in FIG. 5. An organic EL device was prepared by laminating the layer serving as both hole injecting layer and hole transporting layer 3 and 4 and the layer serving as both emission layer and electron transporting layer 5 as the respective coating films, and laminating the hole blocking layer 6 and the cathode thereon by deposition. That is, similar to Example 8, TPA-9 (2) was applied to the ITO substrate by a spin coating method, and dried in a vacuum oven to form the layer serving as both hole injecting layer and hole transporting layer 3 and 4 of about 20 nm thickness.

Subsequently, a coating liquid of PVK (PVK, 2-(4-biphenylyl)-5-(4-t-butylphenyl)-1,3,4-oxadiazole (hereinafter referred to as PBD) and coumarin 6 were dissolved in o-dichlorobenzene in the proportion of 10:3:0.2) was applied by a spin coating method, and dried in a vacuum oven at 100° C. to form the layer serving as both emission layer and electron transporting layer 5 of about 70 nm. Next, bathocuproine (hereinafter referred to as BCP) was deposited to form the hole blocking layer 6. Finally, a mask for cathode deposition was inserted, and an alloy of MgAg was deposited to form the cathode 7.

When current density of 300 mA/cm$^2$ was loaded to the organic EL device thus prepared, a stable green emission of 2800 cd/m$^2$ was obtained.

Example 11

Figure 6:
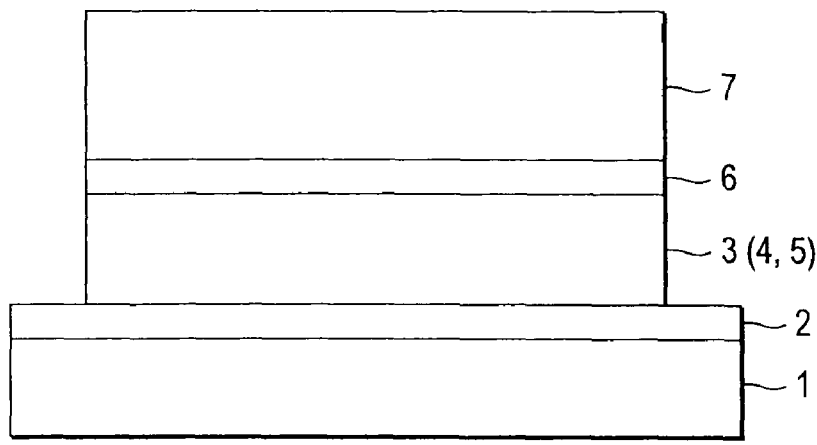
FIG. 6 is a view showing the EL device structure of Example 11.
Figure 7:
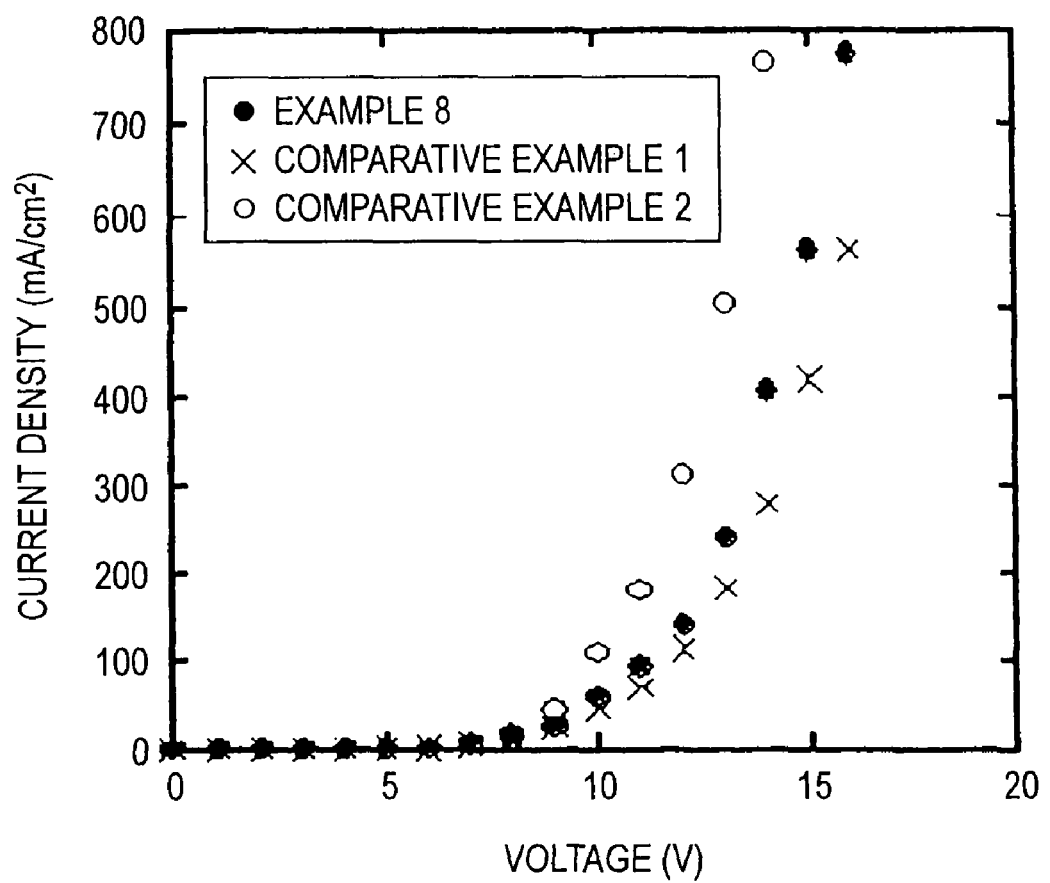
FIG. 7 is a graph comparing the voltage/current density characteristics in Example 8 and Comparative Examples 1 and 2.
Figure 8:
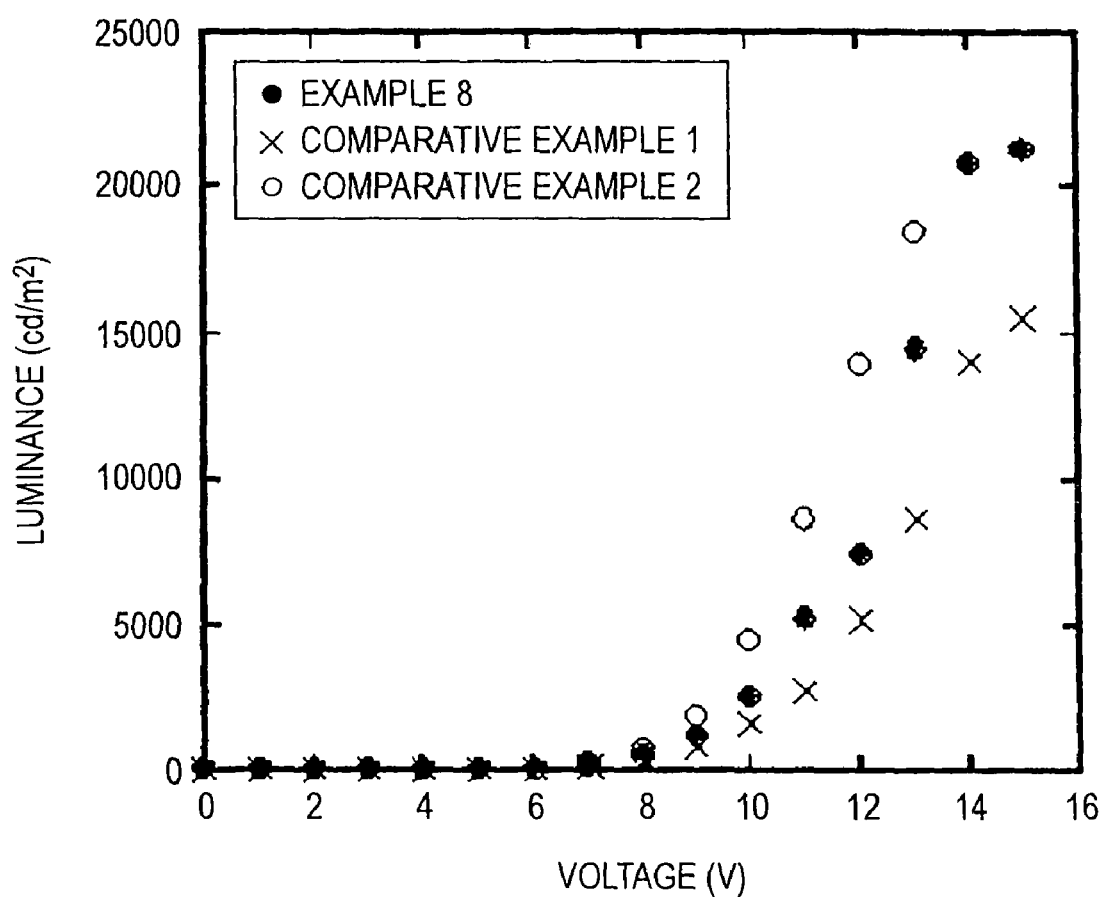
FIG. 8 is a graph comparing the voltage/luminance characteristics in Example 8 and Comparative Examples 1 and 2.
Figure 9:
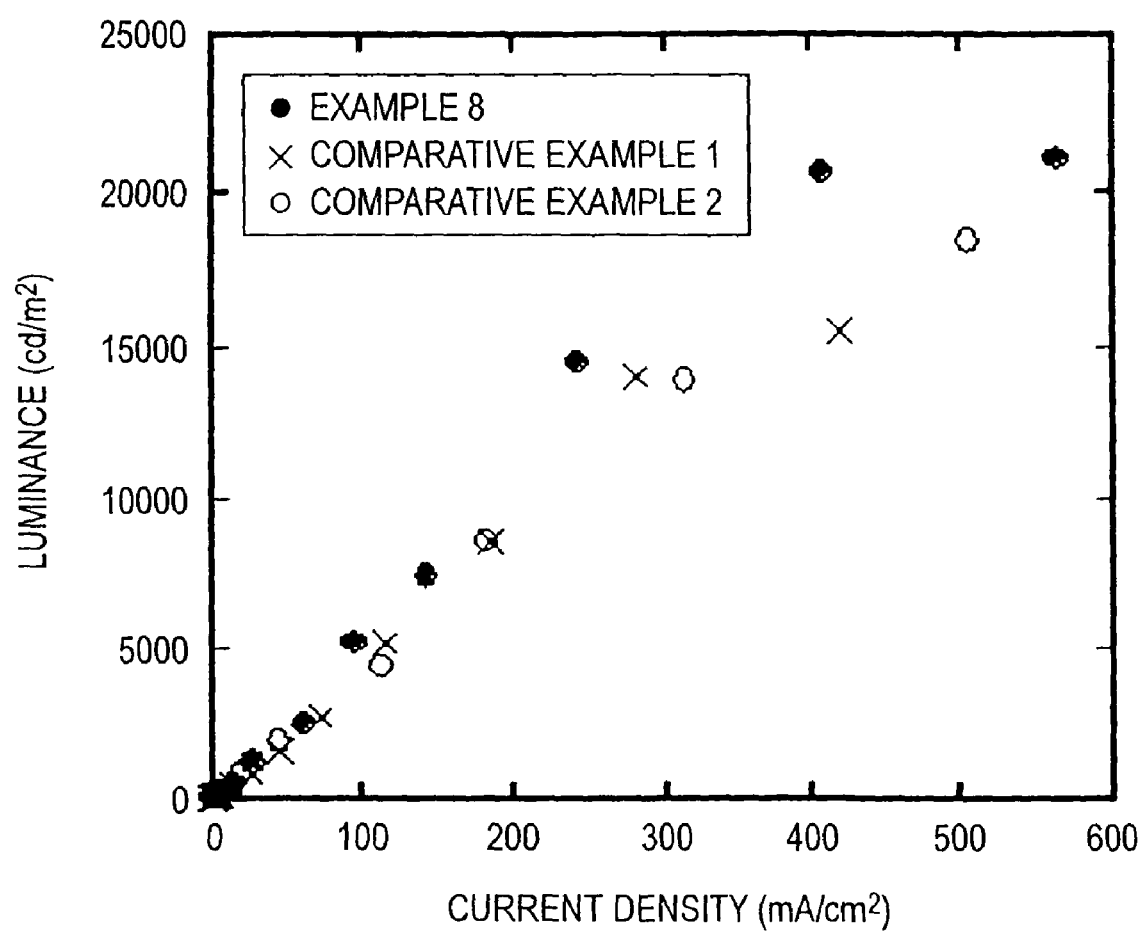
FIG. 9 is a graph comparing the current density/luminance characteristics in Example 8 and Comparative Examples 1 and 2.
Figure 10:
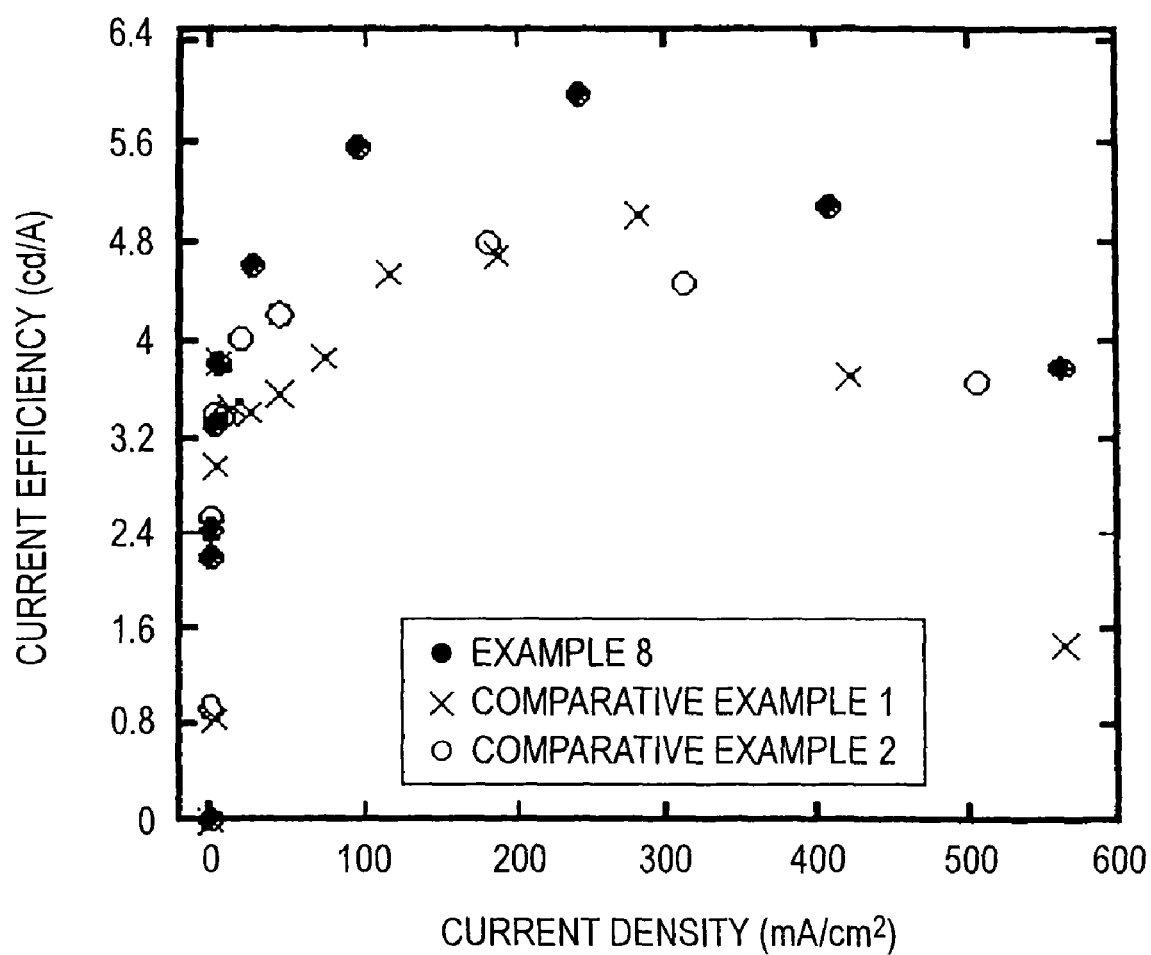
FIG. 10 is a graph comparing the current density/current efficiency in Example 8 and Comparative Examples 1 and 2.
In the drawings, the reference numerals denote the followings.
1: Glass substrate
2: Transparent anode
3: Hole injecting layer
4: Hole transporting layer
5: Layer serving as both emission layer and electron transporting layer
6: Hole blocking layer
7: Cathode

An organic EL device was prepared by forming a layer serving as all of hole injecting layer/hole transporting layer/ emission layer/electron transporting layer 3, 4 and 5 in a form of a coating film, on an ITO electrode previously formed as a transparent anode 2 on a glass substrate 1, and laminating a hole blocking layer 6 and a cathode (aluminum magnesium electrode) 7 by deposition, as shown in FIG. 6.

Subsequently, a coating liquid of TPA-9 (2) (PVK, PBD and coumarin 6 were dissolved in 1,1,2-trichloroethane in the proportion of 10:3:0.2) was applied to the ITO substrate by a spin coating method, and dried in a vacuum oven at 100° C. to form the layer serving as all of hole injection layer/hole transporting layer/emission layer/electron transporting layer 3, 4 and 5. Next, BCP was deposited to form the hole blocking layer 6. Finally, a mask for cathode deposition was inserted, and an alloy of MgAg was deposited to form the cathode 7.

When voltage of 6.3 V was loaded to the organic EL device, a stable green emission of 400 cd/m$^2$ was obtained.

From the above results, it is apparent that emission characteristics and durability of the organic EL device prepared using the arylamine compound of the present invention are superior to the conventional EL device.

While the present invention has been described in detail and with reference to the specific embodiments thereof, it will be apparent to one skilled in the art that various changes and modifications can be made therein without departing from the spirit and scope thereof.

This application is based on Japanese Patent Application No. 2004-089836 filed Mar. 25, 2004 and Japanese Patent Application No. 2004-090334 filed Mar. 25, 2004, the disclosures of which are incorporated herein by reference in their entities.

INDUSTRIAL APPLICABILITY

The arylamine compound having a molecular weight of from 1500 to 6000 of the present invention has high amorphous property, can form a thin film by coating, and is stable in a thin film state, and therefore is excellent as a compound for an organic EL device. By preparing an organic EL device using a thin film obtained by coating the arylamine compound of the present invention as a hole injecting layer or a hole transporting layer, emission efficiency and durability of the conventional coating type organic EL device can remarkably be improved. For example, it became possible to spread the application to home appliances or illumination.

The invention claimed is:

1. An arylamine compound having a molecular weight of from 1500 to 6000 represented by formula (I):

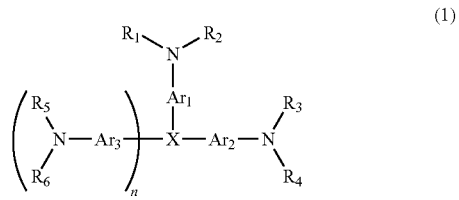

wherein X represents a single bond, CH, CH$_2$, N or NH; Ar$_1$, Ar$_2$ and Ar$_3$ represent a biphenyl group or a terphenyl group; R$_1$, R$_2$, R$_3$, R$_4$, R$_5$ and R$_6$ each independently represent an aryl group, wherein the aryl group may be substituted with a diarylamino group so as to form a triarylamine moiety structure, and further the terminal aryl groups may be substituted with a diarylamino structure group-containing group so as to form a triarylamine sub-structure repeatedly; and n is 0 or 1.

2. The arylamine compound as claimed in claim 1, having 9 or 10 nitrogen atoms in its molecule.

3. The arylamine compound as claimed in claim 2, having 10 nitrogen atoms in its molecule.

4. The arylamine compound as claimed in any one of claims 1 to 3, having from 7 to 9 triarylamine sub-structures in its molecule.

5. An organic electroluminescence device comprising a pair of electrodes, and at least one organic layer interposed therebetween, wherein the device comprises a compound having a molecular weight of from 1500 to 6000 represented by formula (1) as a constituent material of the at least one organic layer:

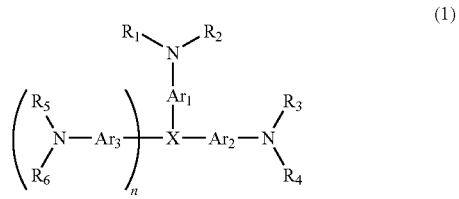

wherein X represents a single bond, CH, CH$_2$, N or NH; Ar$_1$, Ar$_2$ and Ar$_3$ represent a biphenyl group or a terphenyl group; R$_1$, R$_2$, R$_3$, R$_4$, R$_5$ and R$_6$ each independently represent an aryl group, wherein the aryl group may be substituted with a diarylamino group so as to form a triarylamine moiety structure, and further the terminal aryl groups may be substituted with a diarylamono structure group-containing group so as to form a triarylamine sub-structure repeatedly; and n is 0 or 1.

6. The organic electroluminescence device as claimed in claim 5, wherein the arylamine compound has 9 or 10 nitrogen atoms in its molecule.

7. The organic electroluminescence device as claimed in claim 6, wherein the arylamine compound has 10 nitrogen atoms in its molecule.

8. The organic electroluminescence device as claimed in any one of claims 5 to 7, wherein the arylamine compound has from 7 to 9 triarylamine sub-structures in its molecule.

* * * * *